(12) United States Patent
Gershon et al.

(10) Patent No.: US 10,959,923 B2
(45) Date of Patent: *Mar. 30, 2021

(54) PLASMONIC ENHANCEMENT OF ZINC OXIDE LIGHT ABSORPTION FOR SUNSCREEN APPLICATIONS

(71) Applicant: International Business Machines Corporation, Armonk, NY (US)

(72) Inventors: Talia S. Gershon, White Plains, NY (US); Ning Li, White Plains, NY (US); Devendra Sadana, Pleasantville, NY (US); Teodor K. Todorov, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/344,871

(22) Filed: Nov. 7, 2016

(65) Prior Publication Data

US 2017/0065508 A1 Mar. 9, 2017

Related U.S. Application Data

(62) Division of application No. 15/142,816, filed on Apr. 29, 2016.

(60) Provisional application No. 62/213,686, filed on Sep. 3, 2015.

(51) Int. Cl.
| | | |
|---|---|---|
| *A61K 8/27* | (2006.01) | |
| *A61Q 17/04* | (2006.01) | |
| *A61K 8/19* | (2006.01) | |
| *A61K 8/02* | (2006.01) | |
| *A61K 8/04* | (2006.01) | |
| *A61K 8/11* | (2006.01) | |

(52) U.S. Cl.
CPC .............. *A61K 8/27* (2013.01); *A61K 8/0241* (2013.01); *A61K 8/0245* (2013.01); *A61K 8/044* (2013.01); *A61K 8/11* (2013.01); *A61K 8/19* (2013.01); *A61Q 17/04* (2013.01); *A61K 2800/26* (2013.01); *A61K 2800/262* (2013.01); *A61K 2800/413* (2013.01); *A61K 2800/621* (2013.01); *A61K 2800/651* (2013.01); *A61K 2800/805* (2013.01)

(58) Field of Classification Search
None
See application file for complete search history.

(56) References Cited

U.S. PATENT DOCUMENTS

| | | |
|---|---|---|
| 3,761,261 A | 9/1973 | Ono et al. |
| 3,863,007 A | 1/1975 | Warner, Jr. |
| 4,549,195 A | 10/1985 | Bluzer |
| 5,011,782 A | 4/1991 | Lamb |
| 5,028,417 A | 7/1991 | Bhat et al. |
| 5,030,699 A | 7/1991 | Hendrickson |
| 5,147,125 A | 9/1992 | Austin |
| 5,223,250 A | 6/1993 | Mitchell |
| 5,441,726 A | 8/1995 | Mitchnick |
| 5,534,056 A | 7/1996 | Kuehnle |
| 5,553,630 A | 9/1996 | Dupuis et al. |
| 5,902,569 A | 5/1999 | Oshima |
| 5,939,054 A | 8/1999 | Msika et al. |
| 6,419,909 B1 | 7/2002 | Lorant |
| 6,534,044 B1 | 3/2003 | Wada |
| 6,599,355 B1 | 7/2003 | Schmidt |
| 7,143,805 B1 | 12/2006 | Weir |
| 7,241,399 B2 | 7/2007 | Haubold |
| 7,514,863 B2 | 4/2009 | Lee |
| 8,647,373 B1 | 2/2014 | Shepherd |
| 9,056,063 B2 | 6/2015 | Hanson |
| 9,144,535 B1 | 9/2015 | Daly et al. |
| 9,144,536 B1 | 9/2015 | Daly et al. |
| 9,773,931 B2 | 9/2017 | Hossain |
| 2002/0122832 A1* | 9/2002 | Hanke .................... A01N 59/16 424/618 |
| 2003/0102099 A1 | 6/2003 | Yadav |
| 2004/0209081 A1 | 10/2004 | Hagihara |
| 2005/0008861 A1 | 1/2005 | Yadav et al. |
| 2005/0048010 A1 | 3/2005 | Kliss |

(Continued)

FOREIGN PATENT DOCUMENTS

| | | |
|---|---|---|
| CN | 103071535 A | 5/2013 |
| CN | 104609459 A * | 5/2015 |

(Continued)

OTHER PUBLICATIONS

Thokozane Moses Sithole, Synthesis and characterization of MBxOy:Eu (M = Ca, Sr, Ba) phosphors and TiO2 semiconductor for application in luminescence and energy materials, University of the Free State, Nov. 2014.

Sardar et al., Optical-absorption intensities and intermanifold emission cross sections of trivalent erbium ions in calcium fluorophosphate, Journal of Applied Physics, Sep. 2005.

Lu et al., 2008—White Up-Conversion Luminescence in Rare-Earth-Ion-Doped YAlO3 Nanocrystals, J. Phys. Chem. C 2008, 112, 15071-15074.

(Continued)

*Primary Examiner* — Monica A Shin
(74) *Attorney, Agent, or Firm* — Ryan, Mason & Lewis, LLP

(57) ABSTRACT

Zinc oxide compositions as well as techniques for plasmonic enhancement of zinc oxide light absorption for sunscreen applications are provided herein. One example method includes selecting one or more metal particles to be used in conjunction with one or more zinc oxide particles in a sunscreen composition, wherein said selecting is based on the plasmon resonance frequency associated with each of the metal particles, and blending the metal particles and the zinc oxide particles within a medium to create the sunscreen composition.

2 Claims, 1 Drawing Sheet

(56) References Cited

U.S. PATENT DOCUMENTS

| | | |
|---|---|---|
| 2005/0208005 A1 | 9/2005 | Giroud |
| 2005/0227063 A1 | 10/2005 | Lawandy |
| 2005/0238600 A1* | 10/2005 | Lien .................. A61K 8/27 424/70.5 |
| 2005/0265935 A1 | 12/2005 | Hollingsworth |
| 2006/0228310 A1* | 10/2006 | Lyth .................. A61K 8/044 424/59 |
| 2006/0241211 A1 | 10/2006 | Coughlin |
| 2006/0270053 A1 | 11/2006 | Tilak |
| 2007/0280895 A1 | 12/2007 | Weimer |
| 2008/0107695 A1 | 5/2008 | Fleissman |
| 2008/0149850 A1 | 6/2008 | Tardif et al. |
| 2008/0181920 A1 | 7/2008 | Buerger |
| 2008/0220026 A1 | 9/2008 | Maltra |
| 2009/0022765 A1* | 1/2009 | Chung ................ A61K 8/0241 424/401 |
| 2009/0061001 A1 | 3/2009 | Hougaz |
| 2009/0104130 A1 | 4/2009 | Bernstein |
| 2009/0258072 A1 | 10/2009 | Schlossman |
| 2009/0258230 A1 | 10/2009 | Schlossman |
| 2010/0008872 A1 | 1/2010 | Katusic |
| 2010/0040567 A1 | 2/2010 | Katusic |
| 2010/0055138 A1* | 3/2010 | Margulies ............ A61K 8/02 424/401 |
| 2010/0310871 A1 | 12/2010 | McCormick |
| 2011/0268678 A1 | 11/2011 | Armstrong |
| 2013/0006118 A1 | 1/2013 | Pan |
| 2013/0039858 A1 | 2/2013 | Brown |
| 2013/0216834 A1* | 8/2013 | Hashimoto ........... A61K 8/37 428/402 |
| 2014/0142213 A1 | 5/2014 | Weiss |
| 2014/0242129 A1 | 8/2014 | Gaurav |
| 2015/0283059 A1 | 10/2015 | Nagare |
| 2016/0024688 A1 | 1/2016 | Richardson et al. |
| 2016/0030304 A1 | 2/2016 | Nagamatsu et al. |
| 2016/0082513 A1* | 3/2016 | Niedermeyer ......... B22F 9/04 424/405 |

FOREIGN PATENT DOCUMENTS

| | | |
|---|---|---|
| EP | 1889810 A1 | 2/2008 |
| JP | 2008024677 A | 2/2008 |
| WO | 2005023535 A2 | 3/2005 |
| WO | 2008017176 A2 | 2/2008 |
| WO | 2008079758 A1 | 7/2008 |
| WO | WO 2008079758 A1 * | 7/2008 ........... A61K 8/11 |
| WO | 2011004133 A2 | 1/2011 |
| WO | 2011089571 A2 | 7/2011 |
| WO | 2012046204 A1 | 4/2012 |
| WO | 2013040149 | 3/2013 |
| WO | 2013094639 A1 | 6/2013 |
| WO | 2014040177 A1 | 3/2014 |
| WO | 2014049139 A1 | 4/2014 |
| WO | 2014077189 | 5/2014 |
| WO | 2016020168 A1 | 2/2016 |

OTHER PUBLICATIONS

Refractive index of ZnO (Zinc oxide)—Bond-o, http://refractiveindex.info/?shelf=main&book=ZnO&page=Bond-o, Mar. 25, 2016.
Refractive index of SiO2 (Silicon dioxide, Silica, Quartz)—Malitson, http://refractiveindex.info/?shelf=main&book=SiO2&page=Malitson, Mar. 25, 2016.
Schubert et al., Design of multilayer antireflection coatings made from co-sputtered and low-refractive-index materials by genetic algorithm. Optics Express vol. 16, No. 8, 2008.
Law et al., ZnO-Al2O3 and ZnO-TiO2 Core-Shell Nanowire Dye-Sensitized Solar Cells. J. Phys. Chem. B 2006, 110, 22652-22663.
Pu et al., Core/shell structured ZnO/SiO2 nanoparticles: Preparation, characterization and photocatalytic property. Applied Surface Science 257 (2010) 393-397.
Mantz et al., Progress in Organic Coatings 47 (2003) 432-442, "A multiple-scattering model analysis of zinc oxide pigment for spacecraft thermal control coatings.".
Song et al., Toxicology Letters 199 (2010) 389-397, "Role of the dissolved zinc io and reactive oxygen species in cytotoxicity of ZnO nanoparticles.".
Bohren et al., "Absorption and Scattering of Light by Small Particles", Wiley-VCH, © 2004, Weinheim.
Bae et al., J. Phys. Chem. B 2005, 109, 2526-2531, "Comparative Structure and Optical Properties of Ga-, In-, and Sn-Doped ZnO Nanowires Synthesized by thermal evaporation.".
NanoComposix, Silver Nanoparticles: Optical Properties, http://nanocomposix.com/pages/silver-nanoparticles-optical-properties, Apr. 20, 2016.
Awazu et al., 2007—A Plasmonic Photocatalyst Consisting of Silver Nanoparticles Embedded in Titanium Dioxide, J. Am. Chem. Soc. 2008, 130, 1676-1680.
Sherry et al., Localized Surface Plasmon Resonance Spectroscopy of Single Silver Nanocubes, Nano Lett., vol. 5, No. 10, 2005.
Aguirre et al., Ag@ZnO Core_Shell Nanoparticles Formed by the Timely Reduction of Ag+ Ions and Zinc Acetate Hydrolysis in N,N-Dimethylformamide: Mechanism of Growth and Photocatalytic Properties, J. Phys. Chem. C 2011, 115, 24967-24974.
Haynes et al., Nanosphere Lithography: Tunable Localized Surface Plasmon Resonance Spectra of Silver Nanoparticles, J. Phys. Chem. B 2000, 104, 10549-10556.
U. Nobbmann, "FAQ: How important are refractive index & adsorption for nanoparticles?" http://www.materials-talks.com/blog/2014/08/05/faq-how-important-are-refractive-index-absorption-for-nanoparticles/ Materials Talks, Aug. 5, 2014, p. 1-2.
Tsuzuki et al., Nanoparticle Coatings for UV Protective Textiles, RJTA vol. 14 No. 2 2010.
Li et al., Transparent and Light-Emitting Epoxy Super-Nanocomposites Containing ZnO-QDs/SiO2 Nanocomposite Particles as Encapsulating Materials for Solid-State Lighting, J. Phys. Chem. C 2008, 112, 18616-18622.
Li et al., 2011—Sol-gel preparation and characterization of nanoporous ZnO_SiO2 coatings with broadband antireflection properties, Applied Surface Science 257 (2011) 9752-9756.
Messaoudi et al., "Synthesis and characterization of ZnO/Cu2O core-shell nanowires grown by two-step electrodeposition method." Applied Surface Science 343 (2015) 148-152.
Luo et al., Facile synthesis of composition-tuned ZnO/ZnxCd1-xSe nanowires for photovoltaic applications, Nanoscale Research Letters (2015) 10:181.
List of IBM Patents or Applications Treated as Related.
Smijs et al. Titanium Dioxide and Zinc Oxide Nanoparticles in Sunscreens: Focus on Their Safety and Effectiveness, Nanotechnology, Science and Applications 4:95-112, Oct. 2011.
Wikipedia, List of Refractive Indices, last modified Feb. 15, 2017; https://en.wikipedia.org/wiki/List_of_refractive_indices.
Naylor et al. "Sunscreens," accessed 2017, http://telemedicine.org/sundam/sundam2.4.2.html.
Faure, B. et al. Dispersion and Surface Functionalization of Oxide Nanoparticles for Transparent Photocatalytic and UV-protecting Coatings and Sunscreens, Sci Technol. Adv. Mater. 14 2013, 023001.
Ultraviolet Radiation and the INTERSUN Programme [online]. WHO, Nov. 2003 [retrieved on Jun. 8, 2017]. Retrieved from the internet <http://www.who.int/uv/uv_and_health/en/>.
List of IBM Patents of Applications Treated as Related.
Cuprous Oxide, Chemical Book, pp. 1-4, Accessed Sep. 18, 2017, https://www.chemicalbook.com/ProductChemicalPropertiesCB9853041_EN.htm.
Tariq Jan, et al. Sn Doping Induced Enhancement in the Activity of ZnO Nanostructures Against Antibiotic Resistant S. aureus Bacteria; Int J. Nanomedicine, vol. 8, pp. 3679-3687; Published online Sep. 30, 2013.
Bhatti et al. Optical Properties of Chromium & Cobalt Doped Zinc Oxide Powder Prepared by Sol-Gel Combustion Method, with the Assistance of Microwave Radiations; International Journal of Advanced Tech. in Engineering and Science; vol. 3, Issue 10; pp. 80-85; published Oct. 2015.
Family Health Team, "Best Ways to Protect Your Hair From Sun Damage," Cleveland Clinic, health essentials, <https://health.clevelandclinic.org/2014/08/best-ways-to-protect-your-hair-from-sun-damage/>, published Aug. 22, 2014, p. 1-4.

(56) References Cited

OTHER PUBLICATIONS

Machine translation, JP 2008-024677, printer 2018.
Kelly et al. "The Optical Properties of Metal Nanoparticles: The Influence of Size, Shape and Dielectric Environment," Journal of Physical Chemistry B 107:668-677, 2003.
Garcia, "Surface Plasmons in Metallic Nanoparticles: Fundamentals and Applications," Journal of Physics D: Applied Physics 44(28), 283001, 2011.
English language translation of WO 2013 094639 (A1) (Year: 2013).
Simon Aldridge and Anthony Downs. The Group 13 Metals Aluminum, Gallium, Indium and Thallium Chemical Patterns and Peculiarities, 2011 John Wiley & Sons, Ltd., p. 623 (Year: 2011).
Machine translation WO 2011/004133, printed 2017.
Wikipedia "Band Gap" last modified Jul. 18, 2017, https://en.wikipedia.org/wiki/Band_gap.
Machine translation WO 2012/046204, printed 2017.
Latha et al. "Sunscreening Agents: A Review," Journal of Clinical and Aesthetic Dermatology 6(1):16-26, 2013.
Sreejith et al. "Squaraine Dyes: A Mine of Molecular Materials," Journal of Materials Chemistry 18:264-274, 2008.
Merriam-Webster "Roughen." Merriam-Webster.com, Merriam-Webster, n.d. Web. Aug. 22, 2018 (Year: 2018).

\* cited by examiner

PLASMONIC ENHANCEMENT OF ZINC OXIDE LIGHT ABSORPTION FOR SUNSCREEN APPLICATIONS

FIELD

The present application generally relates to chemical technology, and, more particularly, to sunscreen technologies.

BACKGROUND

Sunscreen creams and other such compositions are commonly used to prevent ultraviolet (UV) radiation (also referred to herein as "light" in this context) from reaching the skin of a human user and causing damage. It is noted that UV light is an electromagnetic radiation with a wavelength range between approximately 280 nanometers (nm) and approximately 400 nanometers (specifically, that is the range of UV radiation that is not absorbed by the ozone).

A common active ingredient of existing sunscreen compositions is zinc oxide (ZnO). ZnO is a semiconductor that has a specific band gap, and particles of ZnO used in existing sunscreen compositions are typically approximately 50-200 nm in size. Additionally, in existing sunscreen compositions, typical ZnO materials are capable of absorbing UV light (that is, blocking the UV light from passing through the sunscreen composition to be absorbed by the skin of the user) within a wavelength range of approximately 290 nm through only approximately 350-380 nm.

Additionally, high sun protection factor (SPF) sunscreen compositions, which can absorb a large majority of the UV light in the range of 290-380 nm, require the addition of a higher density of ZnO particles, which causes the composition to become white and/or opaque due to light scattering from the ZnO particles, and which is an often undesirable property to consumers.

SUMMARY

In one embodiment of the present invention, zinc oxide compositions, methods of fabrications thereof and methods of use thereof are provided. An exemplary method can include selecting one or more metal particles to be used in conjunction with one or more zinc oxide particles in a sunscreen composition, wherein said selecting is based on the plasmon resonance frequency associated with each of the metal particles. Such an exemplary method can also include coating at least one portion of the surface of each of the one or more zinc oxide particles with the one or more selected metal particles.

In another embodiment of the invention, a sunscreen composition can include multiple zinc oxide particles suspended within a medium, and one or more metal particles coated on at least one portion of the surface of each of the multiple zinc oxide particles, wherein each of the metal particles comprises a plasmon resonance frequency that supplements the light absorption capabilities of the multiple zinc oxide particles.

Additionally, in another embodiment of the invention, an exemplary method can include selecting one or more metal particles to be used in conjunction with one or more zinc oxide particles in a sunscreen composition, wherein said selecting is based on the plasmon resonance frequency associated with each of the metal particles; and blending the one or more selected metal particles and the one or more zinc oxide particles within a medium to create the sunscreen composition.

In yet another embodiment of the invention, a sunscreen composition can include multiple zinc oxide particles suspended within a medium; and one or more metal particles and the multiple zinc oxide particles blended within the medium, wherein each of the metal particles comprises a plasmon resonance frequency that supplements the light absorption capabilities of the multiple zinc oxide particles.

These and other objects, features and advantages of the present invention will become apparent from the following detailed description of illustrative embodiments thereof, which is to be read in connection with the accompanying drawings.

DETAILED DESCRIPTION

As described herein, an embodiment of the present invention includes ZnO compositions as well as techniques for plasmonic enhancement of ZnO light absorption for sunscreen applications. As further detailed herein, one or more embodiments of the invention include generating ZnO compositions and methods of use thereof for effectively blocking more and/or all of the complete spectrum of UV light (that is, as noted above, the UV radiation that is not absorbed by the ozone, and which ranges between approximately 280 nm and 400 nm) while also preventing whitening effects caused by the scattering of light in the visible spectrum (that is, radiation between approximately 400 nm and 700 nm). As used herein, "scattering" refers to the deflection of rays of visible light from the rays' original path due to interaction with particle surfaces.

As further detailed herein, one or more embodiments of the invention include enhancing the light absorption of ZnO particles by using plasmon resonances. Such an embodiment of the invention can include coating at least one portion of the surface of a ZnO particle (of a sunscreen composition) with one or more metal particles (or nanoparticles) that exhibit plasmon resonances. Different metals have different resonance frequencies, and the metals used in connection with one or more embodiments of the invention can include, for example, silver (Ag) and gold (Au).

In one or more embodiments of the invention, the size of the metal particles used can dictate the resonant energy, wherein smaller particles have higher-energy resonances. Accordingly, in at least one embodiment of the invention, the size of the metal particles used can be less than 30 nm, such as, for example, between 5-10 nm.

As detailed herein, the metal particles themselves attenuate light at their respective resonant frequency. By incorporating the metal particles into the sunscreen formulation, the attenuation of light by ZnO is supplemented by the light attenuation of the plasmonic particles. Accordingly, in one or more embodiments of the invention, UV light is attenuated by the plasmonic metal nanoparticles.

By way merely of example, as the nanoparticle size of a metal such as silver decreases, the wavelength of the resonance blue-shifts. To enhance the absorption of a sunscreen composition/formulation at approximately 400 nm, at least one example embodiment of the invention can include using silver nanoparticles of approximately 10 nm in size.

Figure 1:
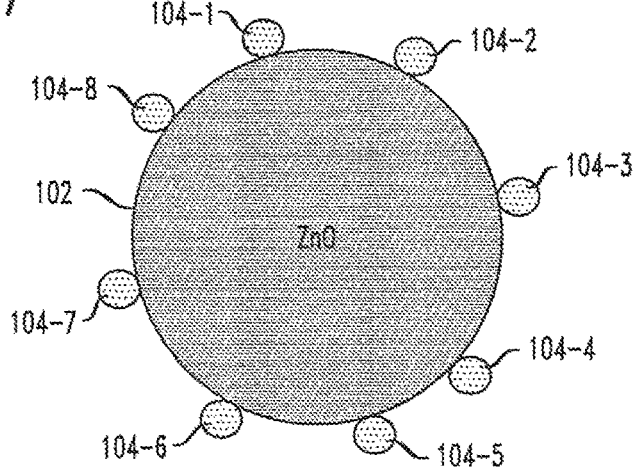
FIG. 1 is a diagram illustrating a ZnO particle coated with multiple metal nanoparticles, according to an example embodiment of the invention.

FIG. 1 is a diagram illustrating a ZnO particle coated with multiple metal nanoparticles, according to an example embodiment of the invention. By way of illustration, FIG. 1 depicts metal nanoparticles 104-1 through 104-8 (collectively, 104) attached to and/or deposited upon a ZnO particle 102 within a sunscreen composition to enhance absorption of the ZnO particle 102 at a resonant frequency. By way of example, silver nanoparticles can be grown directly onto a ZnO particle, using the ZnO particle as a nucleation center. Additionally, in one or more embodiments of the invention, ZnO can be coated onto a metallic silver nanoparticle so as to encase the silver nanoparticle inside of a ZnO particle. One technique for carrying out such an embodiment can include solution approaches. Further, in yet another embodiment of the invention, plasmonic silver nanoparticles can be mixed and/or blended into the ZnO particle sunscreen composition.

As detailed herein, a coating as illustrated in the example embodiment of FIG. 1 can induce a surface plasmon resonance which supplements the light attenuation properties of the ZnO particle 102. Also, in at least one embodiment of the invention, the size of the metal particles/nanoparticles can be selected to create a resonance at a photon energy which is not adequately absorbed by ZnO, so as to complement the oxide's absorption properties. Further, the effect of the metal nanoparticles can be proportional to the number of nanoparticles used.

Figure 2:
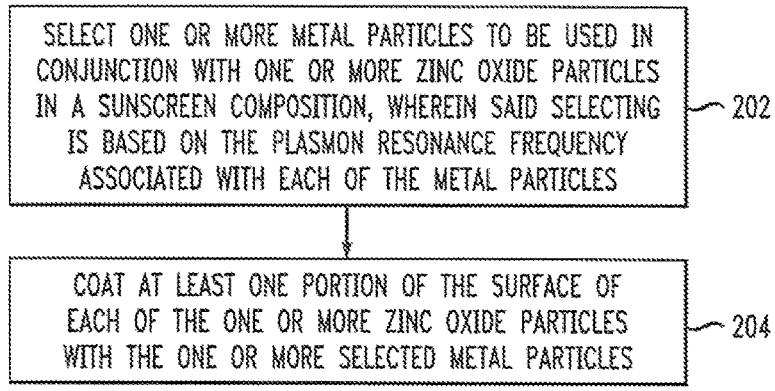
FIG. 2 is a flow diagram illustrating techniques, according to an embodiment of the invention.

FIG. 2 is a flow diagram illustrating techniques, according to an embodiment of the present invention. Step 202 includes selecting one or more metal particles to be used in conjunction with one or more zinc oxide particles in a sunscreen composition, wherein said selecting is based on the plasmon resonance frequency associated with each of the metal particles. The metal particles can include one or more silver particles, one or more gold particles, or a combination of one or more silver particles and one or more gold particles.

Additionally, each of the one or more metal particles can be of a size of less than 30 nanometers. By way of example, in at least one embodiment of the invention, each of the one or more metal particles can be of a size of between five and ten nanometers. Further, in one or more embodiments of the invention, the metal particles can include a number of the metal particles selected based on a desired attenuation magnitude proportional to the number of the metal particles selected.

Step 204 includes coating at least one portion of the surface of each of the one or more zinc oxide particles with the one or more selected metal particles.

Also, an additional embodiment of the invention includes a sunscreen composition that includes multiple zinc oxide particles suspended within a medium, and one or more metal particles coated on at least one portion of the surface of each of the multiple zinc oxide particles, wherein each of the metal particles comprises a plasmon resonance frequency that supplements the light absorption capabilities of the multiple zinc oxide particles.

Figure 3:
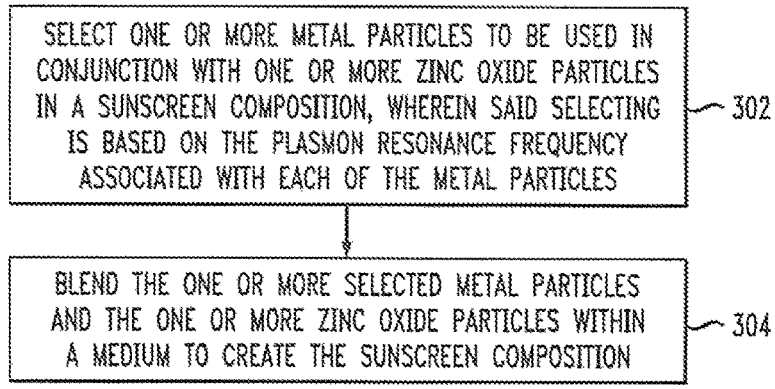
FIG. 3 is a flow diagram illustrating techniques, according to an embodiment of the invention.

FIG. 3 is a flow diagram illustrating techniques, according to an embodiment of the present invention. Step 302 includes selecting one or more metal particles to be used in conjunction with one or more zinc oxide particles in a sunscreen composition, wherein said selecting is based on the plasmon resonance frequency associated with each of the metal particles. The metal particles can include one or more silver particles, one or more gold particles, or a combination of one or more silver particles and one or more gold particles.

Additionally, each of the one or more metal particles can be of a size of less than 30 nanometers. By way of example, in at least one embodiment of the invention, each of the one or more metal particles can be of a size of between five and ten nanometers. Further, in one or more embodiments of the invention, the metal particles can include a number of the metal particles selected based on a desired attenuation magnitude proportional to the number of the metal particles selected.

Step 304 includes blending the one or more selected metal particles and the one or more zinc oxide particles within a medium to create the sunscreen composition.

Also, an additional embodiment of the invention includes a sunscreen composition that includes multiple zinc oxide particles suspended within a medium, and one or more metal particles and the multiple zinc oxide particles blended within the medium, wherein each of the metal particles comprises a plasmon resonance frequency that supplements the light absorption capabilities of the multiple zinc oxide particles.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of another feature, step, operation, element, component, and/or group thereof.

At least one embodiment of the present invention may provide a beneficial effect such as, for example, coating a ZnO particle with one or more metal particles to create a resonance at a photon energy that is not efficiently absorbed by the ZnO particle.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:
1. A sunscreen composition consisting of:
multiple core zinc oxide particles suspended within a medium;
(i) multiple silver particles, each encased in a zinc oxide particle, (ii) one or more silver nanoparticles, and (iii) multiple gold particles, all positioned on a portion of the surface of each of the core zinc oxide particles, wherein the portion is less than the entirety of the surface of each of the core zinc oxide particles, wherein each of the encased silver particles, each of the one or more silver nanoparticles, and each of the gold particles is a size of between five and ten nanometers; and multiple additional zinc oxide particles, wherein the multiple additional zinc oxide particles are blended with the core zinc oxide particles within the medium.

2. A method of creating a sunscreen composition, consisting of:

encasing each of multiple silver particles inside a zinc oxide particle by coating the surface of each of the silver particles with zinc oxide, covering a portion of the surface of each of multiple core zinc oxide particles with (i) the encased silver particles, (ii) one or more silver nanoparticles, and (iii) multiple gold particles by depositing (i) the encased silver particles, (ii) the one or more silver nanoparticles, and (iii) the multiple gold particles on the surface of each of the core zinc oxide particles, wherein the portion is less than the entirety of the surface of the core zinc oxide particles, wherein the core zinc oxide particle is 50-200 nanometers in size, and wherein each of the encased silver particles, each of the one or more silver nanoparticles, and each of the gold particles is a size of between five and ten nanometers; and blending the core zinc oxide particles and one or more additional zinc oxide particles within a medium to create a sunscreen composition.

* * * * *